United States Patent
Gong et al.

[11] Patent Number: 6,140,344
[45] Date of Patent: Oct. 31, 2000

[54] 4-AROYLPIPERIDINE DERIVATIVES-CCR-3 RECEPTOR ANTAGONISTS

[75] Inventors: Leyi Gong, San Mateo; Denis John Kertesz, Mountain View; David Berard Smith, San Mateo; Robert Stephen Wilhelm, Los Altos, all of Calif.

[73] Assignee: Syntex (U.S.A.) Inc., Palo Alto, Calif.

[21] Appl. No.: 09/441,919

[22] Filed: Nov. 17, 1999

Related U.S. Application Data
[60] Provisional application No. 60/108,796, Nov. 17, 1998.

[51] Int. Cl.[7] ............ C07D 215/38; C07D 211/68; A61K 31/445; A61K 31/47; L07D 211/08
[52] U.S. Cl. ............ 514/317; 514/314; 514/318; 546/159; 546/192; 546/193
[58] Field of Search .................. 514/317, 314, 514/318; 546/192, 159, 193

[56] References Cited

U.S. PATENT DOCUMENTS

| | | | |
|---|---|---|---|
| 4,559,349 | 12/1985 | Storni | 514/318 |
| 5,143,923 | 9/1992 | Hrib et al. | 514/321 |
| 5,317,020 | 5/1994 | Emonds-Alt et al. | 514/255 |
| 5,541,201 | 7/1996 | Carr et al. | 514/330 |
| 5,728,835 | 3/1998 | Aoki | 546/194 |

FOREIGN PATENT DOCUMENTS

| | | |
|---|---|---|
| 0 661 266 A1 | 7/1995 | European Pat. Off. |
| 4001 128 | 1/1992 | Japan |
| 2 330 580 | 4/1999 | United Kingdom |
| WO 94/27991 | 12/1994 | WIPO |
| WO 97/48696 | 12/1997 | WIPO |

OTHER PUBLICATIONS

U.S. patent application SN 09/134,013, Filing date Aug. 14, 1998, *Cyclic Amine Derivatives CCR–3 Receptor Antagonists*, Gong, et al. (Assignee Syntex (U.S.A.) Inc); Docket No. R0029B–REG.

*Primary Examiner*—D. Margaret Seaman
*Attorney, Agent, or Firm*—Rohan Peries; Rekha Bansal

[57] ABSTRACT

This invention relates to certain piperidine quaternary salts of Formula (I)

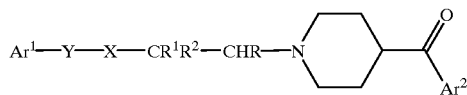

(I)

that are CCR-3 receptor antagonists, pharmaceutical compositions containing them, methods for their use and methods for preparing these compounds.

26 Claims, No Drawings

4-AROYLPIPERIDINE DERIVATIVES-CCR-3 RECEPTOR ANTAGONISTS

CROSS REFERENCE TO RELATED APPLICATIONS

This application claims the benefit under 35 U.S.C. 119(e) of U.S. Provisional Application Ser. No. 60/108,796, filed Nov. 17, 1998, hereby incorporated by reference in its entirety.

FIELD OF THE INVENTION

This invention relates to certain 4-aroylpiperidine derivatives that are CCR-3 receptor antagonists, pharmaceutical compositions containing them, methods for their use and methods for preparing these compounds.

BACKGROUND INFORMATION

Tissue eosinophilia is a feature of a number of pathological conditions such as asthma, rhinitis, eczema and parasitic infections ((see Bousquet, J. et al. *N. Eng. J. Med.* 323: 1033–1039 (1990) and Kay, A. B. and Corrigan. C. J. *Br. Med. Bull.* 48:51–64 (1992)). In asthma, eosinophil accumulation and activation are associated with damage to bronchial epithelium and hyperresponsiveness to constrictor mediators. Chemokines such as RANTES, eotaxin and MCP-3 are known to activate eosinophils ((see Baggiolini, M. and Dahinden, C. A. *Immunol. Today.* 15:127–133 (1994), Rot, A. M. et al. *J. Exp. Med.* 176, 1489–1495 (1992) and Ponath. P. D. et al. *J. Clin. Invest.*, Vol. 97, #3, 604–612 (1996)). However, unlike RANTES and MCP-3 which also induce the migration of other leukocyte cell types, eotaxin is selectively chemotactic for eosinophils ((see Griffith-Johnson, D. A et al. *Biochem. Biophy. Res. Commun.* 197:1167 (1993) and Jose, P. J. et al. *Biochem. Biophy. Res. Commun.* 207, 788 (1994)). Specific eosinophil accumulation was observed at the site of administration of cotaxin whether by intradermal or intraperitoneal injection or aerosol inhalation ((see Griffith-Johnson, D. A et al. *Biochem. Biophy. Res. Commun.* 197:1167 (1993); Jose, P. J. et al. *J. Exp. Med.* 179, 881–887 (1994); Rothenberg, M. E. et al. *J. Exp. Med.* 181, 1211 (1995) and Ponath. P. D. *J. Clin. Invest.*, Vol. 97, #3, 604–612 (1996)).

Glucocorticoids such as dexamethasone, methprednisolone and hydrocortisone have been used for treating many eosinophil-related disorders, including bronchial asthma ((R. P. Schleimer et. al., *Am. Rev. Respir. Dis.*, 141, 559 (1990)). The glucocorticoids are believed to inhibit IL-5, IL-3 mediated eosinophil survival in these diseases. However, prolonged use of glucocorticoids can lead to side effects such as glaucoma, osteoporosis and growth retardation in the patients ((see Hanania N. A et al., *J. Allergy and Clin. Immunol.*, Vol. 96, 571–579 (1995) and Saha M. T. et al, *Acta Paediatrica*, Vol. 86, #2, 138–142 (1997)). It is therefore desirable to have an alternative means of treating eosinophil related diseases without incurring these undesirable side effects.

Recently, the CCR-3 receptor was identified as a major chemokine receptor that eosinophils use for their response to cotaxin, RANTES and MCP-3. When transfected into a murine pre-β lymphoma line, CCR-3 bound eotaxin, RANTES and MCP-3 and conferred chemotactic responses on these cells to eotaxin, RANTES and MCP-3 ((see Ponath. P. D. et al. *J. Exp. Med.* 183, 2437–2448 (1996)). The CCR-3 receptor is expressed on the surface of eosinophils, T-cells (subtype Th-2), basophils and mast cells and is highly selective for eotaxin. Studies have shown that pretreatment of eosinophils with an anti-CCR-3 mAb completely inhibits eosinophil chemotaxis to eotaxin, RANTES and MCP-3 ((see Heath H. et al. *J. Clin. Invest.*, Vol. 99, #2, 178–184 (1997)). Applicants' copending U.S. patent application Ser. No. 09/134,013, filed Aug. 14, 1998 discloses compounds that are CCR-3 antagonists and inhibit eosinophilic recruitment by chemokine such as eotaxin.

Therefore, blocking the ability of the CCR-3 receptor to bind RANTES, MCP-3 and eotaxin and thereby preventing the recruitment of eosinophils should provide for the treatment of eosinophil-mediated inflammatory diseases.

The present invention concerns novel 4-aroylpiperidine analogs which are capable of inhibiting the binding of eotaxin to the CCR-3 receptor and thereby provide a means of combating eosinophil induced diseases, such as asthma.

SUMMARY OF THE INVENTION

In a first aspect, this invention provides compounds selected from the group of compounds represented by Formula (I):

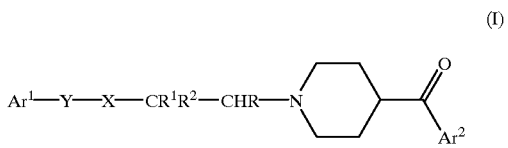

wherein:

$Ar^1$ and $Ar^2$ are, independently of each other, aryl or heteroaryl;

R and $R^1$ are, independently of each other, hydrogen or alkyl;

$R^2$ is an alkyl group of 3 to 6 carbon atoms, heteroalkyl, aryl, aralkyl, heteroaryl, heteroarylalkyl, heterocyclylalkyl, -(alkylene)—C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

X is a group selected from:
(a) —C(O)N($R^3$)—;
(b) —N($R^4$)C(O)N($R^3$)—;
(c) —N($R^4$)C(S)N($R^3$)—;
(d) —SO$_2$N($R^3$)—; or
(e) —N($R^4$)SO$_2$N($R^3$)—;
where:
$R^3$ and $R^4$ are, independently of each other, hydrogen, alkyl, aralkyl, heteroaralkyl, heterocycloalkyl, heteroalkyl, or -(alkylene)—C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy or heteroaralkyloxy; and
Y is a bond or an alkylene chain of 1–3 carbon atoms; and
prodrugs, individual isomers, mixtures of isomers, and pharmaceutically acceptable salts thereof.

In a second aspect, this invention provides pharmaceutical compositions containing a therapeutically effective amount of a compound of Formula (I) or its pharmaceutically acceptable salt and a pharmaceutically acceptable excipient.

In a third aspect, this invention provides a method of treatment of a disease in a mammal treatable by administration of a CCR-3 receptor antagonist, comprising administration of a therapeutically effective amount of a compound of Formula (I) or its pharmaceutically acceptable salt. The disease states include respiratory diseases such as asthma.

In a fourth aspect, this invention provide a process for preparing compounds of Formula (I).

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

"Alkenyl" means a linear unsaturated monovalent hydrocarbon radical of two to six carbon atoms or a branched unsaturated monovalent hydrocarbon radical of three to six carbon atoms, e.g., ethenyl, propenyl, 2-propenyl, pentenyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Acyloxy" means a radical —OC(O)R where R is alkyl or optionally substituted phenyl, e.g., acetoxy, benzoyloxy, and the like.

"Halo" means fluoro, chloro, bromo or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Cycloalkyl" means a saturated monovalent cyclic hydrocarbon radical of three to six ring carbons, e.g., cyclopropyl, cyclohexyl, and the like.

"Monosubstituted-amino" means a radical —NHR where R is alkyl, heteroalkyl, haloalkyl, or optionally substituted phenyl, e.g., methylamino, (1-methylethyl)amino, phenylamino, and the like.

"Disubstituted-amino" means a radical —NRR' where R and R' are independently alkyl, heteroalkyl, haloalkyl, or optionally substituted phenyl. Representative examples include, but are not limited to, dimethylamino, methylethylamino, di(1-methylethyl)amino, and the like.

"Aryl" means a monovalent monocyclic or bicyclic aromatic hydrocarbon radical of 6 to 10 ring atoms and optionally substituted independently with one or more substituents, preferably one, two or three substituents selected from alkyl, haloalkyl, alkenyl, heteroalkyl, halo, cyano, nitro, acyloxy, alkoxy, optionally substituted phenyl, heteroaryl, heteroaralkyl, amino, monosubstituted amino, disubstituted amino, —OR [where R is hydrogen, haloalkyl, optionally substituted phenyl, heteroaryl or heteroaralkyl], —S(O)$_n$R ([where n is an integer from 0 to 2 and R is hydrogen, alkyl, haloalkyl, optionally substituted phenyl, heteroaryl, heteroaralkyl, amino, mono- or disubstituted amino), —NRSO$_2$R' (where R is hydrogen or alkyl and R' is alkyl, amino, mono- or disubstituted amino), —NHC(O)R (where R is hydrogen, alkyl, heteroalkyl, haloalkyl or optionally substituted phenyl), —C(O)R (where R is hydrogen, alkyl, heteroalkyl, haloalkyl or optionally substituted phenyl), —COOR (where R is hydrogen, alkyl, optionally substituted phenyl, heteroaryl or heteroaralkyl), —(alkylene)—COOR (where R is hydrogen, alkyl, optionally substituted phenyl, heteroaryl or heteroaralkyl), methylenedioxy, 1,2-ethylenedioxy, —CONR'R" or —(alkylene)CONR'R" (where R' and R" are independently selected from hydrogen, alkyl, haloalkyl, optionally substituted phenyl, heteroaryl and heteroaralkyl). More specifically the term aryl includes, but is not limited to, phenyl, 1-naphthyl, 2-naphthyl, and derivatives thereof.

"Optionally substituted phenyl" means a phenyl group which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

"Heteroaryl" means a monovalent monocyclic or bicyclic aromatic radical of 5 to 10 ring atoms containing one, two, or three ring heteroatoms selected from N, O, or S, the remaining ring atoms being C. The aromatic radical is optionally substituted independently with one or more substituents, preferably one or two substituents selected from alkyl, haloalkyl, heteroalkyl, halo, cyano, nitro, acyloxy, optionally substituted phenyl, amino, mono- or disubstituted amino, —OR [where R is hydrogen, alkyl, haloalkyl, or optionally substituted phenyl], —S(O)$_n$R [where n is an integer from 0 to 2 and R is hydrogen, alkyl, haloalkyl, optionally substituted phenyl, amino, mono- or disubstituted amino], —NHC(O)R (where R is hydrogen, alkyl, heteroalkyl, haloalkyl or optionally substituted phenyl), —C(O)R (where R is hydrogen, alkyl, heteroalkyl, haloalkyl or optionally substituted phenyl), —COOR (where R is hydrogen, alkyl, or optionally substituted phenyl), —(alkylene)—COOR (where R is hydrogen, alkyl or optionally substituted phenyl), methylenedioxy, 1,2-ethylenedioxy, —CONR'R" or —(alkylene)—CONR'R" (where R' and R" are independently selected from hydrogen, alkyl, haloalkyl, or optionally substituted phenyl). More specifically the term heteroaryl includes, but is not limited to, pyridyl, pyrrolyl, thiophene, pyrazolyl, thiazolyl, imidazolyl, pyrimidinyl, thiadiazolyl, indolyl, carbazolyl, azaindolyl, benzofuranyl, benzotriazolyl, benzisoxazolyl, purinyl, quinolinyl, benzopyranyl, and derivatives thereof.

"Heterocycle" or "Heterocyclyl" means a saturated or unsaturated cyclic radical of 3 to 8 ring atoms in which one or two ring atoms are heteroatoms selected from N, O, or S(O)$_n$ (where n is an integer from 0 to 2). The heterocyclo ring may be optionally substituted independently with one, two or three substituents selected from alkyl, haloalkyl, aryl, aralkyl, heteroaryl, heteroaralkyl, halo, cyano, acyl, amino, monosubstituted amino, disubstituted amino, —COOR (where R is hydrogen or alkyl), —XR (where X is O or S(O)$_n$, where n is an integer from 0 to 2 and R is hydrogen, alkyl, haloalkyl, cycloalkyl, aralkyl, aryl, heteroaryl or heteroaralkyl) or —CONR'R" (where R' and R" are independently selected from hydrogen or alkyl). Representative examples include, but are not limited to, tetrahydropyranyl, piperidino, piperazino, morpholino, 1-(4-chlorophenyl) piperidino, and the like.

"Heteroalkyl" means an alkyl, cycloalkyl, or cycloalkylalkyl radical as defined above, carrying a substituent containing a heteroatom selected from N, O, S(O)$_n$ where n is an integer from 0 to 2. Representative substituents include —NR$^a$R$^b$, OR$^a$ or S(O)$_n$R$^c$, wherein n is an integer from 0 to 2, $R^a$ is hydrogen, alkyl, haloalkyl, optionally substituted phenyl, pyridyl, —COR (where R is alkyl or alkoxy) or aminoalkyl, $R^b$ is hydrogen, alkyl, —SO$_2$R (where R is alkyl or hydroxyalkyl), —SO$_2$NRR' (where R and R' are independently of each other hydrogen or alkyl), —CONR'R", (where R' and R" are independently selected from hydrogen or alkyl) and $R^c$ is hydrogen, alkyl, optionally substituted phenyl, amino, mono- or disubstituted amino. Representative examples include, but are not limited to 2-methoxyethyl, 2-hydroxyethyl, 3-hydroxypropyl, 2-aminoethyl, 3-aminopropyl, 2-methylaminoethyl, 2-dimethylaminoethyl, benzyloxymethyl, and the like.

"Hydroxyalkyl" means a linear monovalent hydrocarbon radical of two to six carbon atoms or a branched monovalent hydrocarbon radical of three or six carbons substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Aminoalkyl" means an alkyl radical as defined above, carrying one or two amino groups, e,g., 2-aminoethyl, 2-aminopropyl, 3-aminopropyl, 1-(aminomethyl)-2-methylpropyl, and the like.

"Aralkyl" means a radical —$R^aR^b$ where $R^a$ is an alkylene group and $R^b$ is an aryl group as defined above e.g., benzyl, phenylethyl, 3-(3-chlorophenyl)-2-methylpentyl, and the like.

"Heteroaralkyl" means a radical —$R^aR^b$ where $R^a$ is an alkylene group and $R^b$ is a heteroaryl group as defined above e.g., pyridin-3-ylmethyl, 3-(benzofuran-2-yl)propyl, and the like.

"Heterocyclylalkyl" means a radical —$R^aR^b$ where $R^a$ is an alkylene group and $R^b$ is a heterocyclyl group as defined above e.g., tetrahydropyran-2-ylmethyl, 4-methylpiperazin-1-ylethyl, and the like.

"Alkoxy", "haloalkyloxy", "aryloxy", "heteroaryloxy", "aralkyloxy", or "heteroaralkyloxy" means a radical —OR where R is an alkyl, haloalkyl, aryl, heteroaryl, aralkyl, or heteroaralkyl respectively as defined above e.g., methoxy, phenoxy, pyridin-2-yloxy, benzyloxy, and the like.

"Optional" or "optionally" means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, when a carbon is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers, such compounds can therefore be produced as individual (R)- or (S)-stereoisomers or as mixtures thereof. For example, if the $R^1$ and $R^2$ substituents in a compound of Formula (I) are different, then the carbon to which they are attached is an asymmetric center and the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable counterion" means an ion having a charge opposite to that of the substance with which it is associated and that is pharmaceutically acceptable. Representative examples include, but are not limited to, chloride, bromide, iodide, methanesulfonate, p-tolylsulfonate, trifluoroacetate, acetate, and the like.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzene-sulfonic acid, 4-chlorobenzenesulfonic acid, 2-napthalenesulfonic acid, 4-toluenesulfonic acid, camphor-sulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Leaving group" has the meaning conventionally associated with it in synthetic organic chemistry i.e., an atom or group capable of being displaced by a nucleophile and includes halogen, alkanesulfonyloxy, arenesulfonyloxy, ester, or amino such as chloro, bromo, iodo, mesyloxy, tosyloxy, trifluorosulfonyloxy, methoxy, N,O-dimethylhydroxyl-amino, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, sulfhydryl or amino group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The nomenclature used in this application is generally based on the IUPAC recommendations, e.g., a compound of Formula (I) where R and $R^1$ are hydrogen, $R^2$ is 2-propyl, $Ar^1$ is 3,4,5-trimethoxyphenyl, $Ar^2$ is 3,4-dichlorophenyl, Y is a bond, and X is —NHCONH— is named as 1-{1-[4-(3,4-dichlorobenzoyl)piperidin-1-ylmethyl]-2-methylpropyl}-3-(3,4,5-trimethoxyphenyl)urea, a compound of Formula (I) where R and $R^1$ are hydrogen, $R^2$ is 2-propyl, $Ar^1$ is 4-methoxyphenyl, $Ar^2$ is 3,4-dichlorophenyl, Y is a bond, and X is —CONH— is named as N-{1-[4-(3,4-dichlorobenzoyl)piperidin-1-ylmethyl]-2-methylpropyl}-4-methoxybenzamide.

Representative compounds of this invention are as follows:

I. Representative compounds of Formula (I) where R=$R^1$=hydrogen; Y=bond; X=—C(O)NH— and other groups are as defined below are:

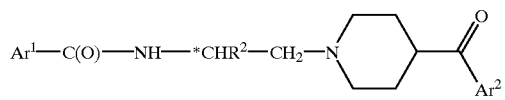

| CPD # | Stereo- chem at *C | $Ar^1$ | $R^2$ | $Ar^2$ | Mass Spec. m/e | M. Pt ° C. |
|---|---|---|---|---|---|---|
| 1 | (RS) | 3,4-methylenedioxyphenyl | 2-propyl | 3,4-dichlorophenyl | 491 | |
| 2 | (RS) | 4-methylphenyl | 2-propyl | 3,4-dichlorophenyl | 461 | 110–118 |
| 3 | (RS) | 4-methoxyphenyl | 2-propyl | 3,4-dichlorophenyl | 477 | |
| 4 | (RS) | 4-vinylphenyl | 2-propyl | 4-fluorophenyl | 422 | |
| 5 | (RS) | 5-methylthiophen-2-yl | 2-propyl | 3,4-dichlorophenyl | 467 | |
| 6 | (RS) | quinolin-3-yl | 2-propyl | 3,4-dichlorophenyl | 498 | |
| 7 | (RS) | 4-acetylphenyl | 2-propyl | 3,4-dichlorophenyl | 489 | |
| 8 | (RS) | 3,4-difluorophenyl | 2-propyl | 3,4-dichlorophenyl | 483 | |
| 9 | (RS) | benzofuran-2-yl | 2-propyl | 3,4-dichlorophenyl | 487 | |
| 10 | (RS) | 4-methoxyphenyl | 2-propyl | 4-fluorophenyl | 426 | |
| 11 | (RS) | 3,4-methylenedioxyphenyl | 2-propyl | 4-fluorophenyl | 440 | |
| 12 | (RS) | 4-acetylphenyl | 2-propyl | 4-fluorophenyl | 438 | |
| 13 | (RS) | 3,4-difluorophenyl | 2-propyl | 4-fluorophenyl | 432 | |
| 14 | (RS) | 4-hydroxymethylphenyl | 2-propyl | 4-fluorophenyl | 426 | |
| 15 | (RS) | 4-dimethylaminophenyl | 2-propyl | 4-fluorophenyl | 439 | |
| 16 | (RS) | 3,4-dimethylphenyl | 2-propyl | 4-fluorophenyl | 424 | |
| 17 | (RS) | 4-methylsulfonylphenyl | 2-propyl | 4-fluorophenyl | | |
| 18 | (RS) | quinolin-3-yl | 2-propyl | 4-fluorophenyl | 447 | |
| 19 | (RS) | 4-methylphenyl | 2-propyl | 4-fluorophenyl | | 123–128 |
| 20 | (RS) | 4-trifluoromethylphenyl | 2-propyl | 4-fluorophenyl | 464 | |
| 21 | (RS) | 5-methylthiophen-2-yl | 2-propyl | 4-fluorophenyl | 416 | |
| 22 | (RS) | benzofuran-2-yl | 2-propyl | 4-fluorophenyl | 436 | |
| 23 | (RS) | 3-amino-4-methylphenyl | 2-propyl | 4-fluorophenyl | 425 | |
| 24 | (RS) | 3-fluoro-4-methylphenyl | 2-propyl | 4-fluorophenyl | 428 | |
| 25 | (RS) | pyridin-2-yl | 2-propyl | 4-fluorophenyl | 397 | |
| 26 | (RS) | 3-bromopyridin-5-yl | 2-propyl | 4-fluorophenyl | | |
| 27 | (RS) | 4-chlorophenyl | 2-propyl | 4-fluorophenyl | | 125–135 |
| 28 | (RS) | 4-methylsulfonylphenyl | 2-propyl | 3,4-dichlorophenyl | 525 | |
| 29 | (RS) | 3-amino-4-methylphenyl | 2-propyl | 3,4-dichlorophenyl | 476 | |
| 30 | (RS) | 4-dimethylaminophenyl | 2-propyl | 3,4-dichlorophenyl | 490 | |
| 31 | (RS) | pyridin-2-yl | 2-propyl | 3,4-dichlorophenyl | 448 | |

II. Representative compounds of Formula (I) where R=R¹=hydrogen; Y=bond; X=—NHC(O)NH— and other groups are as defined below are:

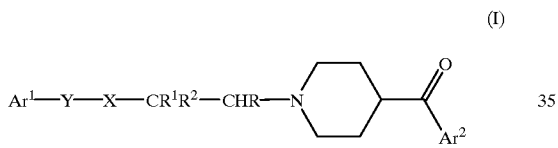

| CPD # | Stereo-chem at *C | Ar¹ | R² | Ar² | Mass Spec. m/e |
|---|---|---|---|---|---|
| 1 | (RS) | 3,4,5-trimethoxyphenyl | 2-propyl | 3,4-dichlorophenyl | 552 |
| 2 | (RS) | 3,5-dimethoxyphenyl | 2-propyl | 3,4-dichlorophenyl | 522 |
| 3 | (RS) | 3-methoxyphenyl | 2-propyl | 3,4-dichlorophenyl | 492 |
| 4 | (RS) | 2,5-dimethoxyphenyl | 2-propyl | 3,4-dichlorophenyl | 522 |
| 5 | (RS) | 3-acetylphenyl | 2-propyl | 3,4-dichlorophenyl | 504 |
| 6 | (RS) | 3-methoxyphenyl | 2-propyl | 4-fluorophenyl | 441 |
| 7 | (RS) | 2,5-dimethoxyphenyl | 2-propyl | 4-fluorophenyl | 471 |
| 8 | (RS) | 3-acetylphenyl | 2-propyl | 4-fluorophenyl | 453 |
| 9 | (RS) | 3,5-dimethoxyphenyl | 2-propyl | 4-fluorophenyl | |
| 10 | (RS) | 3,4,5-trimethoxyphenyl | 2-propyl | 4-fluorophenyl | 501 |
| 11 | (RS) | 3,4,5-trimethoxyphenyl | 2-propyl | phenyl | 483 |

PREFERRED EMBODIMENTS

While the broadest definition of this invention is set forth in the Summary of the Invention, certain compounds of Formula (I) are preferred.

$$Ar^1—Y—X—CR^1R^2—CHR—N\diagup\diagdown—C(O)Ar^2 \quad (I)$$

(I) A preferred group of compounds is that wherein:
R, R¹ are hydrogen.
(A) Within this preferred group, more preferred groups of compounds are those wherein:
(a) X is —C(O)NH—; and
R² is a branched alkylene chain of 3 or 4 carbon atoms, preferably 2-propyl or 2,2-dimethylethyl; or
(b) X is —C(O)NH—; and
R² is heteroalkyl, preferably 1-hydroxyethyl, 2-hydroxyethyl, or 3-hydroxypropyl.

Within these preferred and more preferred groups, even more preferred groups of compounds are those wherein:
(i) Y is a bond; or
(ii) Y is an alkylene chain of 1 or 2 carbon atoms, preferably methylene.

Within the preferred, more preferred groups and even more preferred groups, a particularly preferred group of compounds is that wherein:
Ar¹ is a heteroaryl or aryl ring, preferably a pyridin-2-yl, pyridin-3-yl, quinolin-3-yl or 5-methylthiophen-2-yl ring or a phenyl ring optionally substituted with one, two or three substituents selected from alkyl, heteroalkyl, alkoxy, —COR (where R is alkyl), —SO₂R (where R is alkyl, amino or mono or disubstituted amino), methylenedioxy, hydroxy, halo, acylamino, amino, mono- or disubstituted amino, —CONR'R", —(alkylene)-CONR'R" (where R' and R" are hydrogen or alkyl), —COOR, —(alkylene)—COOR (where R is hydrogen or alkyl) or —NRSO₂R' (where R is hydrogen or alkyl and R' is alkyl, amino, mono or disubstituted amino), more preferably a phenyl ring optionally substituted with one, two or three substituents selected from methyl, methoxy, fluoro, chloro, dimethylamino, acetyl, hydroxy, amino, methylenedioxy, —SO₂Me, 2-acetylaminoethyl, 2-[(R)-amino-3-methylbutyrylamino]ethyl, 2-aminoethyl, aminomethyl, hydroxymethyl, aminocarbonyl, —COOH, carboxymethyl, methoxycarbonylmethyl, aminocarbonylmethyl, dimethylaminocarbonylmethyl, acetylaminomethyl, methylsulfonylamino, methylsulfonylaminomethyl, dimethylaminosulfonylaminomethyl, or dimethylamino, most preferably phenyl, 4-chlorophenyl, 3,4-difluorophenyl, 4-methylphenyl, 4-methoxyphenyl, 4-hydroxyphenyl, 4-dimethylaminophenyl, 4-aminocarbonylphenyl, 4-dimethylaminocarbonylphenyl, 4-acetylphenyl, 4-acetylaminophenyl, 3,4-methylenedioxyphenyl, 4-methylsulfonylphenyl, 4-[(2-acetylamino)ethyl]phenyl, 4-(2-[(R)-amino-3-methylbutyrylamino]ethyl phenyl, 4-(2-aminoethyl)phenyl, 4-(aminomethyl)phenyl, 4-(hydroxymethyl)phenyl, 2,5-dimethoxyphenyl, 3,5-dimethoxyphenyl, 3,4-dimethoxyphenyl, 3,4,5-trimethoxyphenyl, 4-aminocarbonylmethylphenyl, 4-acetylaminomethyphenyl, 4-methylsulfonylaminophenyl, 4-methylsulfonylaminomethylphenyl or 4-aminophenyl; and
Ar² is a heteroaryl or aryl ring, preferably 1-acetylindol-3-yl, 3-methylbenzo-thiophen-2-yl, 5-nitrothiophen-3-yl or a phenyl ring optionally substituted with one, two or three substituents selected from alkyl, heteroalkyl, alkoxy, halo, trifluoromethyl, nitro, or mono- or disubstituted amino, more preferably a phenyl ring substituted with one, or two substituents selected from methyl, methoxy, chloro, fluoro, trifluoromethyl or nitro, most preferably 4-fluorophenyl, 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-fluorophenyl or 3,4-dichlorophenyl.
(B) Another more preferred groups of compounds within the group (I) are those wherein:

(a) X is —NHC(O)N(R³)— wherein R³ is hydrogen, alkyl, or heteroalkyl, preferably hydrogen, methyl, 2-hydroxyethyl, 2-aminoethyl, or 3-hydroxypropyl; and R² is a branched alkylene chain of 3 or 4 carbon atoms, preferably 2-propyl or 2,2-dimethylethyl; or (b) X is —NHC(O)N(R³)— wherein R³ is hydrogen, alkyl or heteroalkyl, preferably hydrogen, methyl, 2-hydroxyethyl, 2-aminoethyl, or 3-hydroxypropyl; and R² is heteroalkyl, preferably 1-hydroxyethyl, 2-hydroxyethyl, or 3-hydroxypropyl.

Within these preferred and more preferred groups, an even more preferred group of compounds is that wherein:
Y is a bond.

Within the preferred, more preferred groups and even more preferred groups, a particularly preferred group of compounds is that wherein:

Ar is a heteroaryl or aryl ring, preferably a pyridin-2-yl, pyridin-3-yl, quinolin-3-yl or 5-methylthiophen-2-yl ring or a phenyl ring optionally substituted with one, two or three substituents selected from alkyl, heteroalkyl, alkoxy, —COR (where R is alkyl), —SO₂R (where R is alkyl, amino or mono or disubstituted amino), methylenedioxy, hydroxy, halo, acylamino, amino, mono- or disubstituted amino, —CONR'R", —(alkylene)—CONR'R" (where R' and R" are hydrogen or alkyl), —COOR, —(alkylene)—COOR (where R is hydrogen or alkyl) or —NRSO₂R' (where R is hydrogen or alkyl and R' is alkyl, amino, mono or disubstituted amino), more preferably a phenyl ring optionally substituted with one, two or three substituents selected from methyl, methoxy, fluoro, chloro, dimethylamino, acetyl, acetylamino, hydroxy, amino, methylenedioxy, —SO₂Me, 2-acetylaminoethyl, 2-[(R)-amino-3-methylbutyrylamino]ethyl, 2-aminoethyl, aminomethyl, hydroxymethyl, aminocarbonyl, —COOH, carboxymethyl, methoxycarbonylmethyl, aminocarbonylmethyl, dimethylaminocarbonylmethyl, acetylaminomethyl, methylsulfonylamino, methylsulfonylaminomethyl, dimethylaminosulfonylaminomethyl, or dimethylamino, most preferably phenyl, 3-methoxyphenyl, 3-methylsulfonylphenyl, 3-dimethylaminophenyl, 3-acetylaminophenyl, 3-acetylphenyl, 3-[(2-acetylamino)ethyl]-phenyl, 3-aminocarbonylphenyl, 3-carboxyphenyl, 2,5-dimethoxyphenyl, 3,5-dimethoxyphenyl, 3,4-dimethoxyphenyl, 3,4,5-trimethoxyphenyl, 3-aminocarbonylmethylphenyl, 3-acetylaminomethyphenyl, 3-carboxymethylphenyl, 3-methylsulfonylaminophenyl, 3-methylsulfonylaminomethylphenyl or 3-aminophenyl; and Ar² is a heteroaryl or aryl ring, preferably 1-acetylindol-3-yl, 3-methylbenzo-thiophen-2-yl, 5-nitrothiophen-3-yl or a phenyl ring optionally substituted with one, two or three substituent selected from alkyl, heteroalkyl, alkoxy, halo, trifluoromethyl, nitro, or mono- or disubstituted amino, more preferably a phenyl ring substituted with one, or two substituents selected from methyl, methoxy, chloro, fluoro, trifluoromethyl or nitro, most preferably 4-fluorophenyl, 3,4-difluorophenyl, 4-nitrophenyl, 4-trifluoromethylphenyl, 4-chlorophenyl, 2,3-dichlorophenyl, 3-methyl-4-nitrophenyl, 3-chloro-4-fluorophenyl or 3,4-dichlorophenyl.

GENERAL SYNTHETIC SCHEME

The compounds of the present invention can be prepared in a number of ways known to one skilled in the art. Preferred methods include, but are not limited to, the general synthetic procedures described below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as *Fieser and Fieser's Reagents for Organic Synthesis*, Volumes 1–15 (John Wiley and Sons, 1991); *Rodd's Chemistry of Carbon Compounds,* Volumes 1–5 and Supplementals (Elsevier Science Publishers, 1989), *Organic Reactions*, Volumes 1–40 (John Wiley and Sons, 1991), *March's Advanced Organic Chemistry,* (John Wiley and Sons, 1992), and *Larock's* Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Preparation of Compounds of Formula (I)

A compound of Formula (I) where R, R¹, R², X, Y, Ar¹ and Ar² are as defined in the Summary of the invention is prepared as illustrated in Scheme A below.

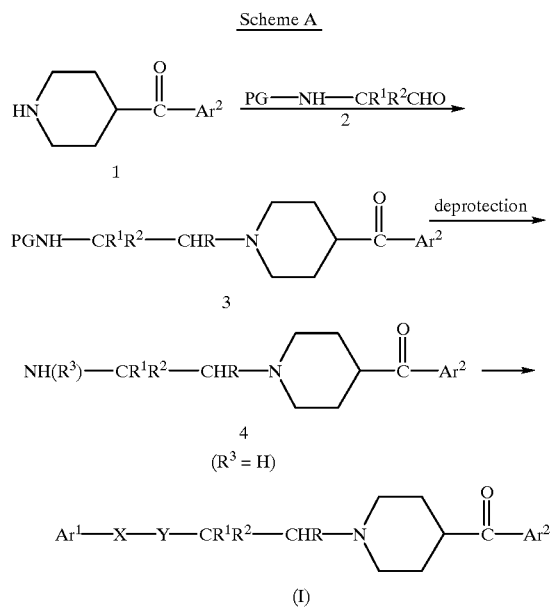

In general, compounds of formula 3 are prepared in two steps by first converting a 4-aroylpiperidine of formula 1 to an N-protected aminoalkyl derivative of formula 3, followed by removal of the amino protecting group in 3 as described in detail below.

An N-protected aminoalkyl derivative of formula 3 [where PG is an amino protecting group [(e.g., tert-butoxycarbonyl (BOC), benzyloxycarbonyl (CBZ), benzyl, and the like)] is prepared by reacting a compound of formula 1 with an aldehyde of formula 2 under reductive amination reaction conditions i.e., in the presence of a suitable reducing agent (e.g., sodium cyanoborohydride, sodium triacetoxyborohydride, and the like) and with or without an organic acid (e.g., glacial acetic acid, trifluoroacetic acid, and the like) at ambient temperature. Suitable solvents for the reaction are halogenated hydrocarbons (e.g., 1,2-dichloroethane, chloroform, and the like).

A 4-aroylpiperidine 1 such as 4-(4-fluorobenzoyl) piperidine is commercially available. 4-(3,4-Dichlorobenzoyl)piperidine can be prepared by the procedure described in Boswell et. al., *J. Med. Chem.* 21, 136, (1977). Compound 1 can also be prepared from N-tert-butoxycarbonyl-4-piperidone whose synthesis is described in Scheme F below by removal of the tert-butoxycarbonyl group by methods well known in the art.

An aldehyde of formula 2 is conveniently prepared from the corresponding N-protected natural or unnatural α-amino acid esters by reduction of the ester group to an aldehyde group with a suitable reducing agent such as DIBAL-H®. Alternatively, it can be prepared by oxidation of the alchohol group in N-protected α-amino alcohols such as valinol.

Generally, α-amino acid esters are either commercially available. For example, alanine methyl ester, serine methyl ester, valine ethyl ester are commercially available. Other α-amino acid esters can be prepared by esterification of α-amino acids by methods well known in the art. Both natural and unnatural amino acids are commercially available from vendors such as Aldrich and Bachem. Examples of unnatural amino acids include, homoserine, homocysteine, N-α-methylargininc, norleucine, N-methylisoleucine, phenylglycine, hydroxyproline, pyroglutamine, ornithine, 2-aminoisobutyric acid, 2-aminobutyric acid, β-cyclohexylalanine, 3-(1-naphthyl) alanine, 3-(2-naphthyl)alanine, citrulline, pipecolinic acid, piperazic acid, 4-chlorophenylalanine, 4-fluorophenylalanine and sarcosine.

The N-protected aminoalkyl derivative 3 is converted to a compound of formula 4 by removal of the amino protecting group. The conditions utilized depend on the nature of the protecting group. For example, if the protecting group is the tert-butoxycarbonyl group it is removed under acidic hydrolysis reaction condition whereas if it is the benzyl group it is removed under catalytic hydrogenation reaction conditions.

A compound of formula 4 where $R^3$ is other than hydrogen can be prepared, if desired, by alkylating the corresponding compound of formula 4 where $R^3$ is hydrogen with an alkylating agent $R^3L$ where L is a leaving group under alkylating conditions such as halo, tosylate or mesylate.

A compound of formula 4 is then converted to a compound of Formula (I) by procedures well known in the art. Some such procedures are described below.

1. Compounds of Formula (I) where X is —C(O)N($R^3$)—, and Y and $Ar^1$ are defined in the Summary of the Invention are prepared as described in Scheme B below:

Scheme B

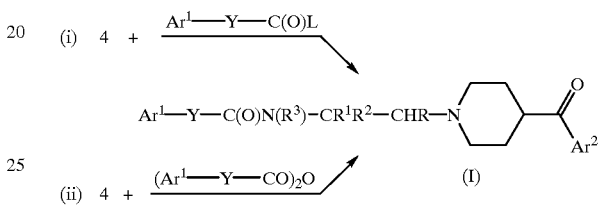

A compound of Formula (I) where X is an amido group can be prepared, either:
(i) by reacting a compound of formula 4 with an acylating reagent $Ar^1$—Y—C(O)L, where L is a leaving group under acylating conditions, such as a halo (particularly Cl or Br) or imidazolide. Suitable solvents for the reaction include aprotic solvents (e.g., dichloromethane, THF, dioxane and the like). When an acyl halide is used as the acylating agent the reaction is carried out in the presence of a non-nucleophilic organic base (e.g., triethylamine or pyridine, preferably pyridine); or
(ii) by heating a compound of formula 4 with an acid anhydride. Suitable solvents for the reaction are tetrahydrofuran, dioxane and the like.

2. Compounds of Formula (I) where X is —N($R^4$)C(O)N ($R^3$)—, —N($R^4$)C(S)N($R^3$)—, and Y and $Ar^1$ are defined in the Summary of the Invention are prepared as described in Scheme C below:

Scheme C

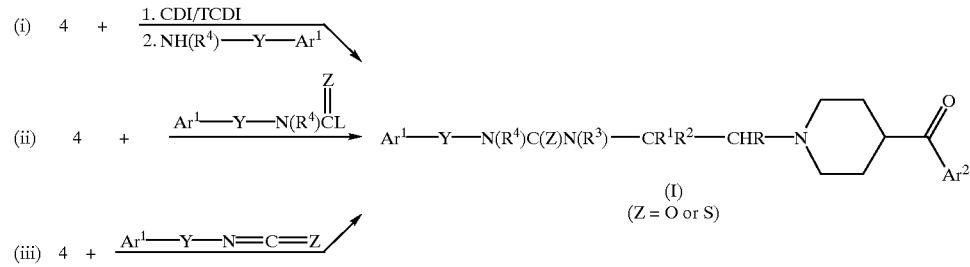

A compound of Formula (I) where X is a urea/thiourea group can be prepared, either:
(i) by reacting a compound of formula 4 with an activating agent such as carbonyl diimidazole/thiocarbonyl diimidazole, followed by nucleophilic displacement of the imidazole group with a primary or secondary amine. Suitable solvents include polar organic solvents (e.g., tetrahydrofuran, dioxane and the like);

(ii) by reacting a compound of formula 4 with a carbamoyl/thiocarbamoyl halide. The reaction is carried out in the presence of a non-nucleophilic organic base. Suitable solvents for the reaction are dichloromethane, 1,2-dichloroethane, tetrahydrofuran or pyridine; or (iii) by reacting a compound of formula 4 with an isocyanate/isothiocyanate in an aprotic organic solvent (e.g., benzene, tetrahydrofuran, dimethylformamide and the like).

3. Compounds of Formula (I) where X is —SO$_2$N(R$^3$)— are prepared as described in Scheme D below:

Scheme D

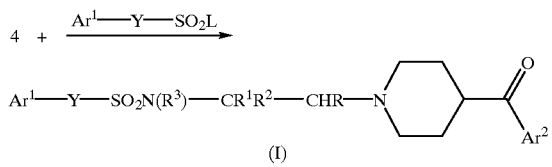

A compound of Formula (I) where X is a sulfonamido group can be prepared by reacting a compound of formula 4 with a sulfonyl halide, utilizing the reaction conditions described in method (i) of Scheme B. Sulfonyl halides are commercially available or may be prepared by methods such as those described in (1) Langer, R. F.; *Can. J. Chem.* 61, 1583–1592, (1983); (2) Aveta, R.; et. al.; *Gazetta Chimica Italiania,* 116, 649–652, (1986); (3) King, J. F. and Hillhouse, J. H.; *Can. J. Chem.;* 54, 498, (1976); and (4) Szymonifka, M. J. and Heck, J. V.; *Tet. Lett.;* 30, 2869–2872, (1989).

4. Compounds of Formula (I) where X is —N(R$^4$)SO$_2$N (R$^3$ are prepared as described in Scheme E below:

Scheme E

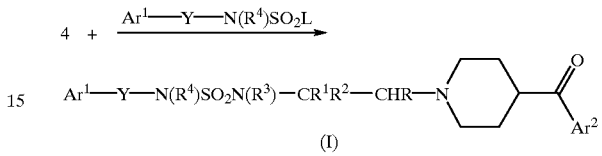

A compound of Formula (I) where X is a sulfamide group can be prepared by reacting a compound of formula 4 with a sulfamoyl halide, utilizing the reaction conditions described in method (i) of Scheme B. Sulfamoyl halides are commercially available or may be prepared by methods such as those described in Graf, R; German Patent, 931225 (1952) and Catt, J. D. and Matler, W. L.; *J. Org. Chem.,* 39, 566–568, (1974).

Alternatively, a compound of Formula (I) where R, R$^1$, R$^2$, X, Y, Ar$^1$ and Ar$^2$ are as defined in the Summary of the invention is prepared as illustrated in Scheme F below.

Scheme F

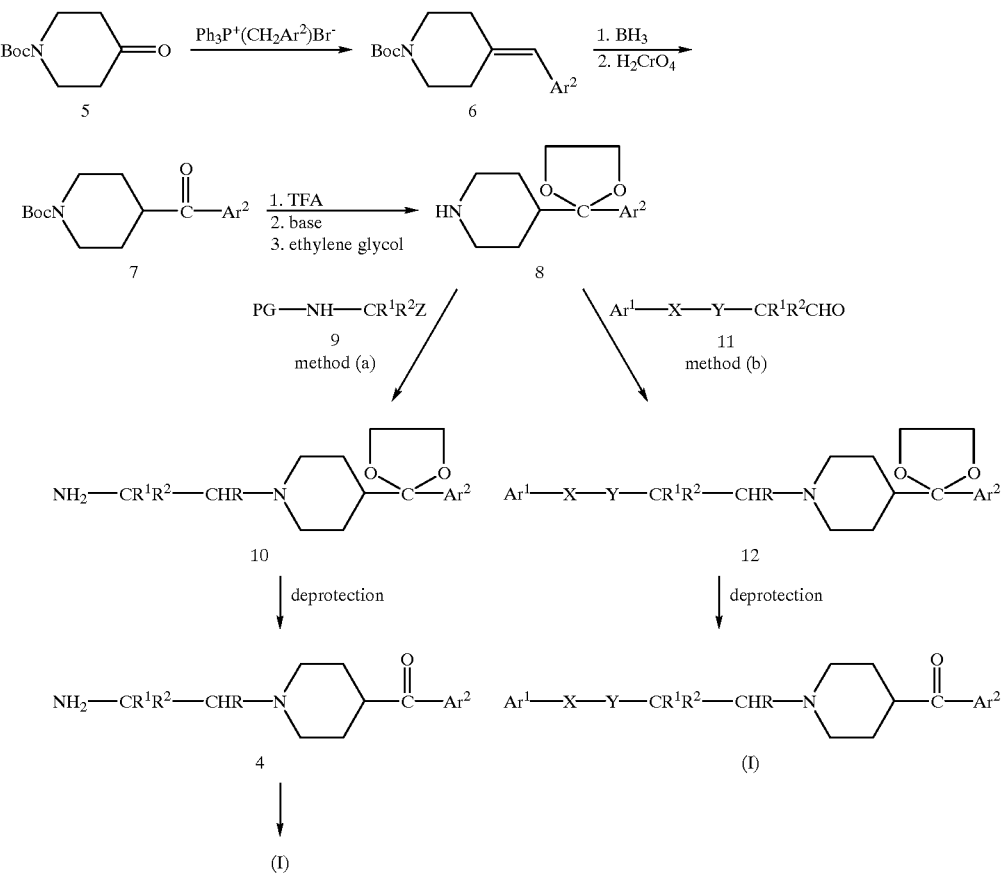

Condensation of Boc-protected piperidone of formula 5 with a Wittig reagent of formula $Br^-(Ph)_3P^+$—$CH_2Ar^2$ in the presence of a suitable base such as n-butyllithium provides an alkylidene intermediate of formula 6. Treatment of 6 with borane, followed by oxidation of the resulting alkylborane with an oxidizing agent such as chromic acid under the reaction conditions described in Brown, Garg *J Am. Chem. Soc.* 83, 2951 (1961) provides the Boc-protected -4-aroylpiperidine of formula 7. Removal of the Boc protecting group with a suitable acid such as trifluoroacetic acid, followed by basic work up provides the corresponding 4-aroylpiperidine. The keto group in 4-aroylpiperidine is protected as the cyclic ketal by reaction with ethylene glycol to give a compound of formula 8 which is then converted to a compound of Formula (I) by methods (a) or (b) as described below.

Method (a):

Reaction of 8 with a compound of formula 9 where PG is an amino protecting group [(e.g., tert-butoxycarbonyl (BOC), benzyloxycarbonyl (CBZ), benzyl, and the like)] and Z is an aldehyde, ketone (X=—C(O)R where R is alkyl), carboxy or a reactive carboxy derivative e.g., acid halide, provides an aminoalkylpiperidine of formula 10.

The reaction conditions employed for the preparation of 10 depend on the nature of the Z group. If Z is an aldehyde or a ketone group, the reaction is carried out under reductive amination reaction conditions i.e., in the presence of a suitable reducing agent (e.g., sodium cyanoborohydride, sodium triacetoxyborohydride, and the like) and an organic acid (e.g., glacial acetic acid, trifluoroacetic acid, and the like) at ambient temperature. Suitable solvents for the reaction are halogenated hydrocarbons (e.g., 1,2-dichloroethane, chloroform, and the like). If Z is a carboxy group, the reaction is carried out in the presence of a suitable coupling agent [e.g., N,N-dicyclohexylcarbodiimide, 1-(3-dimethylamino-propyl)-3-ethylcarbodiimide, and the like] in a suitable organic solvent (e.g., methylene chloride, tetrahydrofuran, and the like) to give an amide intermediate. Deprotection of the amino group, followed by reduction of the amide intermediate with a suitable reducing agent (e.g., diborane, lithium aluminum hydride, and the like) in an ethereal organic solvent such as ether or tetrahydrofuran then provides a compound of formula 10. If Z is an acid derivative such as an acid chloride, the reaction is carried out in the presence of a suitable base such as triethylamine, pyridine in an organic solvent (e.g., methylene chloride, dichloroethane, N,N-dimethylformamide, and the like) to give an amide intermediate which is reduced to compound 10 as described above.

In general, compounds of formula 9 are commercially available or they can be prepared by methods well known in the field of organic chemistry. Some examples of such procedures are illustrated and described in detail below.

An aldehyde of formula 9 (Z is a —CHO) is conveniently prepared from the corresponding natural or unnatural α-amino acids of formula 9 where Z is a carboxy group by first preparing the corresponding ester by methods well known in the art, followed by reduction of the ester group to an aldehyde group with a suitable reducing agent such as DIBAL-H®. Alternatively, it can be prepared from N-protected α-amino alcohol by oxidation of the hydroxy group with a suitable oxidising agent.

A ketone of formula 9 can be prepared from the N-protected α-amino acids of formula 9 by converting the α-amino acids 9 to a Weinreb amide, followed by treatment with a Grignard reagent of formula RMgBr where R is an alkyl group. Alternatively, it can be prepared by alkylating the corresponding aldehyde of formula 9 (Z is —CHO) with a Grignard reagent, followed by oxidation of the resulting alcohol with a suitable oxidizing agent such as potassium permanganate, and the like.

Compounds of formula 9 where Z is an acid derivative e.g., an acid chloride can be prepared from the corresponding acids of formula 9 (Z is —COOH) by chlorinating the carboxy group with a suitable chlorinating agent (e.g., oxalyl chloride, thionyl chloride and the like) in a suitable organic solvent such as methylene chloride and the like.

Hydrolysis of the ketal group in 10 provides a compound of formula 4 which is then converted to a compound of Formula (I), utilizing the procedures in Schemes A–E above.

Method (b):

Alternatively, a compound of Formula (I) is prepared by condensing a compound of formula 8 with an aldehyde of formula 11 where X, Y and $Ar^1$ are as defined in the Summary of the Invention under reductive amination reaction conditions to provide a compound of formula 12 followed by hydrolysis of the ketal group with a suitable acid such as hydrochloric acid, and the like.

Compounds of formula 11 are prepared from commercially available α-amino alcohols by following the procedures described in Schemes B–E above, followed by oxidation of the alcohol group to the aldehyde with a suitable oxidizing agent such as pyridinium chlorochromate.

Utility, Testing and Administration

General Utility

The compounds of the invention are CCR-3 receptor antagonists and therefore they should inhibit recruitment of eosinophil, T cells, basophils and mast cells by chemokines such as RANTES, eotaxin and MCP-3. The compounds of the present invention are, in general, more potent than the corresponding piperidine analogs wherein $R^1$ and $R^2$ are hydrogen. Therefore, compounds of this invention and compositions containing them are useful in the treatment of cosiniphil-induced diseases such as asthma, rhinitis, eczema, and parasitic infections in mammals, especially humans.

Testing

The CCR-3 antagonistic activity of the compounds of this invention may be measured by in vitro assays such as ligand binding and chemotaxis assays as described in more detail in Examples 5, 6, and 7. It can be assayed in vivo by Ovalbumin induced Asthma in Balb/c Mice Model as described in more detail in Example 8.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.05–20 mg per kilogram body weight of the recipient per day; preferably about 0.1–10 mg/kg/day. Thus, for administration to a 70 kg person, the dosage range would most preferably be about 7 mg to 0.7 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences,* edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 4.

EXAMPLES

The following preparations and examples are given to enable those skilled in the art to more clearly understand and to practice the present invention. They should not be considered as limiting the scope of the invention, but merely as being illustrative and representative thereof. Detailed descriptions of the synthesis of compounds of Formula (I) have been given in copending U.S. application Ser. No. 09/134,013, filed Aug. 14, 1998 whose disclosure is hereby incorporated by reference.

Synthetic Examples

Example 1

1-{1-[4-(3,4-Dichlorobenzoyl)piperidin-1-ylmethyl]-2-methylpropyl}-3-(3,4,5-trimethoxyphenyl)urea

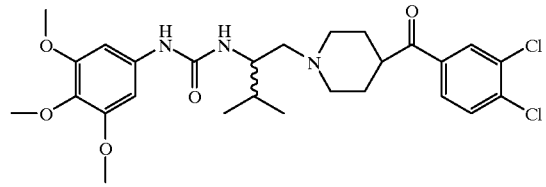

Step 1

A mixture of 4-(3,4-dichlorobenzoyl)piperidine (1.28 g, 4.96 mmol) (see., Boswell et. al., *J. Med. Chem.,* 21, 136, (1977)) and DL-N-BOC-Valinal (1.33 g, 6.6 mmol) (see., Stanfield et. al., *J. Org. Chem.,* 46(23), 4797, (1981)) in dichloromethane (150 mL) was treated with sodium triacetoxyborohydride (1.36 g, 6.4 mmol). The reaction mixture was stirred under nitrogen for 1 day, then directly purified by filtration through a pad of silica gel by elution with hexanes and ethyl acetate. The organics were removed and the resultant oil (2.1 g) was dissolved in dichloromethane (22 mL) and treated with trifluoroacetic acid (8 mL). After stirring under nitrogen for 1 h, the solvent was removed in vacuo. The residue was treated with aqueous sodium bicarbonate until basic and the product was extracted into chloroform. The organic layer was dried with magnesium sulfate, filtered and concentrated to give [1-(2-amino-3-methylbutyl)piperidin-4-yl]-(3,4-dichlorophenyl)methanone (1.47 g) as an oil.

Step 2

A solution of [1-(2-amino-3-methylbutyl)piperidin-4-yl]-(3,4-dichlorophenyl)methanone (30 mg) in dichloromethane (3 mL) was treated with trimethoxyphenyl-isocyanate (30 mg) and triethylamine (1 mL, 0.3 M in dichloromethane) was added and the reaction mixture was stirred at ambient temperature overnight. A polystyrene trisamine resin (approx. 0.5 g, 3.5 mmol/g) was added to capture excess isocyanate, and stirring was continued for an additional 2 h. The resin was filtered and the filtrate was concentrated. Purification by column chromatography gave 1-{1-[4-(3,4-dichloro-benzoyl)piperidin-1-ylmethyl]-2-methylpropyl}-3-(3,4,5-trimethoxyphenyl)urea (27.5 mg).

Example 2

N-{1-4-(3,4-Dichlorobenzoyl)piperidin-1-ylmethyl]-2-methylpropyl}-4-methoxybenzamide

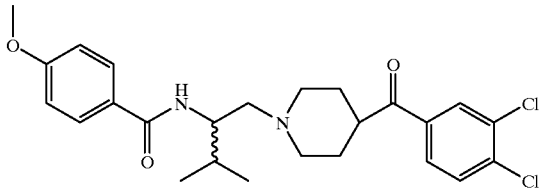

Step 1

A solution of 1-(2-amino-3-methylbutyl)piperidin-4-yl]-(3,4-dichlorophenyl)methanone (30 mg) in dichloromethane (3 mL) was treated with 4-methoxybenzoyl chloride (30 mg). Triethylamine (1 mL, 0.3M in dichloromethane) was then added and the reaction mixture was stirred at ambient temperature overnight. A polystyrene trisamine resin (approx. 0.5 g, 3.5 mmol/g) was added to capture excess acid chloride, and stirring was continued for an additional 2 h. The resin was filtered and the filtrate was concentrated. Purification by column chromatography gave N-{1-[4-(3,4-dichloro-benzoyl)piperidin-1-ylmethyl]-2-methylpropyl}-4-methoxybenzamide (34.8 mg).

Example 3

N-{1-[4-(3,4-Dichlorobenzoyl)piperidin-1-ylmethyl]-2-methylpropyl}-4-methylbenzamide

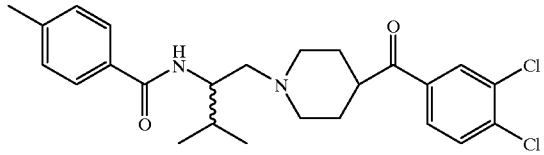

Step 1 n-Butyllithium (43.2 mL, 2M in pentane, 108 mmol) was slowly added to an ice-cooled suspension of 3,4-dichlorobenzyl triphenylphosphonium bromide (54 g, 108 mmol) (prepared by stirring equimolar amounts of 3,4 dichlorobenzyl bromide and triphenylphosphine in THF at 65° overnight) in dry THF (500 mL) under an argon atmosphere. After 15 min., the reaction mixture was allowed to warm to room temperature, and was stirred for an additional 2 h. 1-tert-Butoxycarbonyl-4-piperidone (21.42 g, 108 mmol) was added and the stirring was continued overnight. Hexane (2 L) was added and the reaction was stirred and then filtered. The filtrate was concentrated in vacuo to give 41.8 g of an orange gum. Column chromatography on 0.5 kg flash grade silica, eluting with a gradient of 70% methylene chloride/hexane through 100% methylene chloride, followed by a gradient of 1% methanol/methylene chloride through 5% methanol/methylene chloride gave 1-(tert-butoxycarbonyl)-4-(3,4-dichloro-benzylidene)piperidine (29 g) as a light tan oil.

Step 2

To a room temperature solution of 1-(tert-butoxycarbonyl)-4-(3,4-dichlorobenzylidene)piperidine (6.4 g, 18.7 mmol) in dry THF (100 mL) under argon was added diborane (22.4 ml, 1 M in THF, 22.4 mmol) and the reaction mixture was stirred for 3 h. Water (20 ml) was slowly added dropwise to kill excess diborane. Tetrahydrofuran was remove in vacuo and ether (200 mL) was added. The reaction mixture was cooled in an ice bath and Jones reagent (take 18.6 g sodium dichromate hydrate, 14 mL conc. sulfuric acid and add enough water to make 93 mL solution) was added dropwise at a rate such that the reaction temperature stayed at about 25° C. The orange solution was stirred at room temperature 2 h. The organic layer was separated and the aqueous layer was extracted twice with ether. The combined organic layers were washed twice with dilute aqueous potassium carbonate solution, dried over anhydrous magnesium sulfate, and the organics were removed. The crude reaction mixtures was flash chromatographed on flash silica gel with a gradient of 10% ethyl acetate/hexane through 15% ethyl acetate/hexane to give 4-(3,4-dichlorobenzoyl)piperidine-1-carboxylic acid tert-butyl ester (3.8 g, 10.6 mmol).

Step 3

To a room temperature solution of 4-(3,4-dichlorobenzoyl)piperidine-1-carboxylic acid tert-butyl ester (3.8 g, 10.6 mmol) in methylene chloride (100 mL) was added trifluoroacetic acid (25 mL) and the solution was stirred for 1 h. After removing the organics, ethyl acetate (200 mL) was added and the resulting solution was basified with 1N aqueous sodium hydroxide solution. The ethyl acetate layer was separated, dried with magnesium sulfate and concentrated to give 4-(3,4-dichlorobenzoyl)piperidine (2.73 g) as a white solid.

Step 4

A mixture of 4-(3,4-dichlorobenzoyl)piperidine (1.0 g, 3.9 mmol), ethylene glycol (0.65 ml, 11.6 mmol), p-toluenesulfonic acid mono hydrate (1.48 g, 7.8 mmol), and toluene (100 mL) was refluxed through a Dean-Stark trap for 4 h. After concentration, the residue was stirred with ethyl acetate and dilute aqueous sodium bicarbonate solution. The organic layer was separated, dried over magnesium sulfate, and concentrated in vacuo to give 4-[2-(3,4-dichlorophenyl)-[1,3]dioxolan-2-yl]piperidine (0.6 g, 1.99 mmol).

Step 5

Diisopropylethyl amine (17.4 mL, 134 mmol) was added a solution of (DL)-valinol (9.85 g, 95 mmol) in methylene chloride (100 ml). The reaction mixture was cooled to 0° C., treated with a solution of p-toluoyl chloride (12.8 mL, 91 mmol) in methylene chloride (50 mL) and then allowed to warm to room temperature. After stirring for 3 h, excess aqueous sodium hydroxide solution was added and the reaction was transferred to a separatory funnel. The organic layer was separated and the aqueous layer washed with one portion of methylene chloride. The combined organic layers were washed with water and brine, dried over magnesium sulfate and concentrated in vacuo. Chromatography eluting with 25% ethyl acetate in hexanes, followed by 50% ethyl acetate in hexanes gave N-p-toluoyl valinol (18.04 g).

Step 6

Dimethylsulfoxide (2.2 mL, 31 mmol) was slowly added via syringe to a stirred −78° C. solution of oxalyl chloride (15 mL, 171 mmol) in methylene chloride (35 mL) under inert atmosphere. After 10 min., a solution of N-p-toluoyl valinol (6.0 g, 29 mmol) in methylene chloride (50 mL) was added and the stirring was continued for additional 15 min. Triethylamine was added (6 mL, 389 mmol) and the reaction was allowed to warm to ambient temperature. After 1.5 h, the reaction was diluted with 50% ethyl acetate in hexanes and washed with water and brine. Filtration through a pad of silica gel and subsequent solvent removal left a solid residue. Chromatography eluting with 20% ethyl acetate in hexanes, then 33% ethyl acetate in hexanes gave N-p-toluoyl valinaldehyde (3.6 g) as a solid, which was utilized in Step 7.

Step 7

A solution of 4-[2-(3,4-dichlorophenyl)-[1,3]dioxolan-2-yl]piperidine (0.21 g, 0.7 mmol), N-p-toluoyl valinaldehyde (0. 17g, 0.764 mmol), sodium triactetoxy-borohydride (0.22 g, 1.04 mmol) in methylene chloride (20 mL) was stirred overnight under argon. After concentrating the reaction mixture, the residue was stirred with ethyl acetate and dilute aqueous potassium carbonate solution. The organic layer was separated and the aqueous layer was extracted with ethyl acetate. The combined organic layers were dried over magnesium sulfate and concentrated in vacuo. The crude was flash chromatographed on flash silica gel with 1% methanol/methylene chloride (containing 1% ammonia) to give N-(1-{4-[2-(3,4-dichlorophenyl)-[1,3 ]dioxolan-2-yl]piperidin-1-yl-methyl}-2-methylpropyl)-4-methylbenzamide (0.187g, 0.366 mmoles).

Step 8

A mixture of N-(1-{4-[2-(3,4-dichlorophenyl)-[1,3]dioxolan-2-yl]piperidin-1-yl-methyl}-2-methylpropyl)-4-methylbenzamide (0.4 g, 0.791 mmol), aqueous HCl (10 mL, 6 N), and acetonitrile (10 mL) was refluxed for 2 h. After concentrating the reaction mixture, the residue was stirred with ethyl acetate and water. Sodium hydroxide solution (6 N) was added until the aqueous layer was pH 8. The organic layer was separated and the aqueous layer was extracted with ethyl acetate. The combined organics were dried over magnesium sulfate and concentrated to give N-{1-[4-(3,4-dichlorobenzoyl)-piperidin-1-ylmethyl]-2-methylpropyl}-4 -methylbenzamide which was converted to the hydrochloride salt by adding 2 molar excess ethereal HCl (1 M) to an ether solution of the free base.

Example 4

Formulation Examples

The following are representative pharmaceutical formulations containing a compound of Formula (I).

Tablet formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable formulation

The following ingredients are mixed to form an injectable formulation.

| Ingredient | Amount |
| --- | --- |
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

Topical formulation

A topical formulation is prepared with the following ingredients.

| Ingredient | Amount, g |
| --- | --- |
| compound of this invention | 10 |
| Span 60 | 2 |
| TWEEN ® 60 | 2 |
| mineral oil | 5 |
| petrolatum | 10 |
| methyl paraben | 0.15 |
| propyl paraben | 0.05 |
| BHA (butylated hydroxy anisole) | 0.01 |
| water | q.s. to 100 |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
| --- | --- |
| Witepsol ® H-15 | balance |

Example 5

CCR-3 Receptor Binding Assay-In Vitro

The CCR-3 antagonistic activity of the compounds of the invention was determined by their ability to inhibit the binding of $^{125}$I eotaxin to CCR-3 L1.2 transfectant cells obtained from LeukoSite (Cambridge, Mass.).

The assay was performed in Costar 96-well polypropylene round bottom plates. Test compounds were dissolved in DMSO and then diluted with binding buffer (50 mM HEPES, 1 mM $CaCl_2$, 5 mM $MgCl_2$, 0.5% bovine serum albumin, 0.02% sodium azide, pH 7.24) such that the final DMSO concentration was 2%. 25 μl of the test solution or only buffer with DMSO (control samples) was added to each well, followed by the addition of 25 g 1 of $^{125}$I-eotaxin 100 pmol) (NEX314, New England Nuclear, Boston, Mass.) and 1.5×10$^5$ of the CCR-3 L1.2 transfected cells in 25 μl binding buffer. The final reaction volume was 75 μl.

After incubating the reaction mixture for 1 h at room temperature, the reaction was terminated by filtering the reaction mixture through polyethylenimine treated Packard Unifilter GF/C filter plate (Packard, Chicago, Ill.). The filters were washed four times with ice cold wash buffer containing 10 mm HEPES and 0.5M sodium chloride (pH 7.2) and dried at 65° C. for approximately 10 min. 25 μl/well of Microscint-20™ scintillation fluid (Packard) was added and the radioactivity retained on the filters was determined by using the Packard TopCount™.

Compounds of this invention were active in this assay.

The $IC_{50}$ value (concentration of test compound required to reduce $^{125}$I-eotaxin binding to the CCR-3 L 1.2 transfected cells by 50%) for compounds in Tables I and II was between 0.6 to 10 μm.

Example 6

Inhibition of Eotaxin Mediated Chemotaxis of CCR-3 L1.2 Transfectant Cells—In vitro Assay The CCR-3 antagonistic activity of the compounds of this invention can be determined by measuring the inhibition of eotaxin mediated chemotaxis of the CCR-3 L1.2 transfectant cells, using a slight modification of the method described in Ponath, P. D. et al., 1996. "Cloning of the Human Eosinophil Chemoattractant, Eotaxin". *J. Clin. Invest.* 97: 604–612. The assay is performed in a 24-well chemotaxis plate (Collaborative Biomedical Products). The CCR-3 L1.2 transfectant cells, designated as 10E6, are grown in culture medium containing RPMI 1640, 10% Hyclone™ fetal calf serum, 5.5%×10$^{-5}$ 2-mercaptoethanol and G 418 (0.8 mg/ml). 18–24 hours before the assay, the transfected cells are treated with n-butyric acid at a final concentration of 5 mM/1×10$^6$ cells/ml, isolated and resuspended at 1×10$^7$ cells/ml in assay medium containing equal parts of RPMI 1640 and M199 with 0.5% BSA.

Human eotaxin suspended in PBS (Gibco # 14190-029) at 1 mg/ml is added to bottom chamber in a final concentration of 100 nm. Biocoat™ Transwell culture inserts (Costar Corp., Cambridge Mass.) having 3 micron pore size were inserted into each well and L1.2 cells (1×10$^6$) are added to the top chamber in a final volume of 100 μl. Test compounds in DMSO are added both to the top and bottom chambers such that the final DMSO volume was 0.5%. The assay is performed against two sets of controls. Positive control contained cells with no test compound in the top chamber and only eotaxin in the lower chamber. Negative control contained cells with no test compound in the top chamber and neither eotaxin nor test compound in lower chamber. The plate is incubated at 37° C. After 4 h, the inserts are removed from the chambers and the cells that have migrated to the bottom chamber are counted by pipetting out 500 μl of the cell suspension from the lower chamber to 1.2 ml Cluster tubes (Costar) and counting them on a FACS for 30 sec.

Compounds of this invention are active in this assay.

Example 7

Inhibition of Eotaxin Mediated Chemotaxis of Human Eosinophils—In Vitro Assay

The ability of compounds of the invention to inhibit eotaxin mediated chemotaxis of human eosinophils can be assessed using a slight modification of procedure described in Carr, M. W. et al., *Proc. Natl. Acad. Sci. USA,* 91: 3652–3656 (1994). Experiments are performed using 24 well chemotaxis plates (Collaborative Biomedical Products). Eosinophils are isolated from blood using the procedure described in PCT Application, Publication No. WO 96/22371. The endothelial cells that should be used are the endothelial cell line ECV 304 that can be obtained from European Collection of Animal Cell Cultures (Porton Down, Salisbury, U.K.). Endothelial cells are cultured on 6.5 mm diameter Biocoat® Transwell tissue culture inserts (Costar Corp., Cambridge Mass.) with a 3.0 μM pore size. Culture media for ECV 304 cells consists of M 199, 10% Fetal Calf Serum, L-glutamine and antibiotics. Assay media consists of equal parts RPMI 1640 and M 199, with 0.5% BSA. 24 h before the assay 2×10$^5$ ECV 304 cells are plated on each insert of the 24-well chemotaxis plate and incubated at 37° C. 20 nM of eotaxin diluted in assay medium is added to the bottom chamber. The final volume in bottom chamber was 600 μl. The endothelial coated tissue culture inserts are inserted into each well. 10$^6$ eosinophil cells suspended in 100 μl assay buffer are added to the top chamber. Test compounds dissolved in DMSO are added to both top and bottom chambers such that the final DMSO volume in each well is 0.5%. The assay is performed against two sets of controls. Positive control contains cells in the top chamber and eotaxin in the lower chamber. Negative control contains cells in the top chamber and only assay buffer in the lower chamber. The plates are incubated at 37° C. in 5% $CO_2$/95% air for 1–1.5 h.

The cells that have migrated to the bottom chamber are counted using flow cytometry. 500 μl of the cell suspension from the lower chamber is placed in a tube, and relative cell counts is obtained by acquiring events for a set time period of 30 seconds.

Compounds of this invention are active in this assay.

Example 8

Inhibition of Eosinophil Chemotaxis by CCR-3 Antagonist in Ovalbumin Sensitized Balb/c Mice— In Vivo Assay The CCR-3 antagonistic activity of the compounds of the invention can be determined by measuring the inhibition of eosinophil accumulation into the BAL fluid of Ovalbumin (OA)-sensitized balb/c mice after antigen challenge by aerosol. Briefly, male balb/c mice weighing 20–25 g are sensitized with OA (10 μg in 0.2 ml aluminum hydroxide solution) intraperitoneally on days 1 and 14. After a week, the mice are divided into ten groups. Test compounds or vehicle (positive control group) are administered. After 1 h, the mice are placed in a Plexiglass box and exposed to OA aerosol generated by a PARISTAR™ nebulizer for 20 min. Mice which have not been sensitized or challenged are included as negative control. After 24 or 72 h, the mice are anesthetized (urethane, approx. 1 g/kg, i.p.), a tracheal cannula (PE 60 tubing) is inserted and the lungs are lavaged four times with 0.3 ml PBS. The Bal fluid is transferred into plastic tubes and kept on ice. Total leukocytes in a 20 μl aliquot of the BAL fluid is determined by hemocytometer and/or Coulter Counter™. Differential leukocyte counts are made on Cytospin preparations which have been stained with a modified Wright's stain (Diff-Quick™) by light microscopy using standard morphological criteria.

Compounds of this invention are expected to be active in this assay.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound selected from compounds of Formula (I):

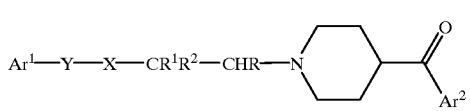

(I)

wherein:
Ar$^1$ and Ar$^2$ are, independently of each other, aryl or heteroaryl;
R and R$^1$ are, independently of each other, hydrogen or alkyl;
R$^2$ is an alkyl group of 3 to 6 carbon atoms, heteroalkyl, aryl, aralkyl, heteroaryl, heteroarylalkyl, heterocyclylalkyl, —(alkylene)—C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy or heteroaralkyloxy;
X is a group selected from:
(a) —C(O)N(R$^3$)—;
(b) —N(R$^4$)C(O)N(R$^3$)—;
(c) —N(R$^4$)C(S)N(R$^3$)—;
(d) —SO$_2$N(R$^3$)—; or
(e) —N(R$^4$)SO$_2$N(R$^3$)—;
where:
R$^3$ and R$^4$ are, independently of each other, hydrogen, alkyl, aralkyl, heteroaralkyl, heterocycloalkyl, heteroalkyl, or —(alkylene)—C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy or heteroaralkyloxy; and
Y is a bond or an alkylene chain of 1–3 carbon atoms; and prodrugs, individual isomers, mixtures of isomers, and pharmaceutically acceptable salts thereof.

2. The compound of claim 1 wherein R$^2$ is a branched alkyene chain of 3 or 4 carbon atoms.

3. The compound of claim 2 wherein:
R and R$^1$ are hydrogen; and
X is —C(O)N(R$^3$)— wherein R$^3$ is hydrogen, alkyl or heteroalkyl.

4. The compound of claim 3 wherein:
Ar$^1$ is a heteroaryl ring; and
Ar$^2$ is an aryl ring.

5. The compound of claim 3 wherein:
Ar$^1$ and Ar$^2$ are aryl.

6. The compound of claim 4 wherein:
X is —C(O)NH—;
Y is a bond; and
R$^2$ is 2-propyl or 2,2-dimethylethyl.

7. The compound of claim 6 wherein:
Ar$^1$ is pyridin-2-yl, pyridin-3-yl, quinolin-3-yl or 5-methylthiophen-2-yl; and
Ar$^2$ is is a phenyl ring optionally substituted with one, two or three substituent(s) selected from alkyl, heteroalkyl, alkoxy, halo, trifluoromethyl, nitro, or monosubstituted or disubstituted amino.

8. The compound of claim 7 wherein:
Ar$^2$ is 3,4-difluorophenyl, 2,3-dichlorophenyl, 3,4-dichlorophenyl or 4-fluorophenyl.

9. The compound of claim 5 wherein:
X is —C(O)NH—;
Y is a bond; and
R$^2$ is 2-propyl or 2,2-dimethylethyl.

10. The compound of claim 9 wherein:
Ar$^1$ is a phenyl ring optionally substituted with one, two or three substituents selected from alkyl, heteroalkyl, alkoxy, —COR (where R is alkyl), —SO$_2$R (where R is alkyl, amino or mono or disubstituted amino), methylenedioxy, hydroxy, halo, acylamino, amino, mono- or disubstituted amino, —CONR'R", —(alkylene)—CONR'R" (where R' and R" are hydrogen or alkyl), —COOR, —(alkylene)—COOR (where R is hydrogen or alkyl) or —NRSO$_2$R' (where R is hydrogen or alkyl and R' is alkyl, amino, mono or disubstituted amino); and
Ar$^2$ is is a phenyl ring optionally substituted with one, two or three substituent(s) selected from alkyl, heteroalkyl, alkoxy, halo, trifluoromethyl, nitro, or monosubstituted or disubstituted amino.

11. The compound of claim 10 wherein:
Ar$^1$ is a phenyl ring optionally substituted with one, two or three substituents selected from methyl, methoxy, fluoro, chloro, dimethylamino, acetyl, hydroxy, amino, methylenedioxy, —SO$_2$Me, 2-acetylaminoethyl, 2-[(R)-amino-3-methylbutyrylamino]ethyl, 2-aminoethyl, aminomethyl, hydroxymethyl, aminocarbonyl, dimethylaminocarbonyl, —COOH, carboxymethyl, methoxycarbonylmethyl, aminocarbonylmethyl, dimethylaminocarbonylmethyl, acetylaminomethyl, methylsulfonylamino, methylsulfonylaminomethyl, dimethylaminosulfonylaminomethyl, or dimethylamino; and
Ar$^2$ is 3,4-difluorophenyl, 2,3-dichlorophenyl, 3,4-dichlorophenyl or 4-fluorophenyl.

12. The compound of claim 11 wherein Ar$^1$ is phenyl, 4-chlorophenyl, 3,4-difluorophenyl, 4-methylphenyl, 4-methoxyphenyl, 4-hydroxyphenyl, 4-dimethylaminophenyl, 4-aminocarbonylphenyl, 4-dimethylaminocarbonylphenyl, 4-acetylphenyl, 4-acetylaminophenyl, 3,4-methylenedioxyphenyl, 4-methylsulfonylphenyl, 4-[(2-acetylamino)ethyl]phenyl, 4-{2-[(R)-amino-3-methylbutyrylamino]ethyl}phenyl, 4-(2-aminoethyl)phenyl, 4-(aminomethyl)phenyl, 4-(hydroxymethyl)phenyl, 2,5-dimethoxyphenyl, 3,5-dimethoxyphenyl, 3,4-dimethoxyphenyl, 3,4,5-trimethoxyphenyl, 4-aminocarbonylmethylphenyl, 4-acetylaminomethyphenyl, 4-methylsulfonyl-aminophenyl, 4-methylsulfonylaminomethylphenyl or 4-aminophenyl.

13. The compound of claim 2 wherein:
R and $R^1$ are hydrogen; and
X is —NHC(O)N($R^3$)— wherein $R^3$ is hydrogen, alkyl or heteroalkyl.

14. The compound of claim 13 wherein:
$Ar^1$ is a heteroaryl ring; and
$Ar^2$ is an aryl ring.

15. The compound of claim 13 wherein:
$Ar^1$ and $Ar^2$ are aryl.

16. The compound of claim 14 wherein:
X is —NHC(O)NH—;
Y is a bond; and
$R^2$ is 2-propyl or 2,2-dimethylethyl.

17. The compound of claim 16 wherein:
$Ar^1$ is pyridin-2-yl, pyridin-3-yl, quinolin-3-yl or 5-methylthiophen-2-yl; and
$Ar^2$ is is a phenyl ring optionally substituted with one, two or three substituent(s) selected from alkyl, heteroalkyl, alkoxy, halo, trifluoromethyl, nitro, or monosubstituted or disubstituted amino.

18. The compound of claim 17 wherein:
$Ar^2$ is 3,4-difluorophenyl, 2,3-dichlorophenyl, 3,4-dichlorophenyl or 4-fluorophenyl.

19. The compound of claim 15 wherein:
X is —NHC(O)NH—;
Y is a bond; and
$R^2$ is 2-propyl or 2,2-dimethylethyl.

20. The compound of claim 19 wherein:
$Ar^1$ is a phenyl ring optionally substituted with one, two or three substituents selected from alkyl, heteroalkyl, alkoxy, —COR (where R is alkyl), —$SO_2R$ (where R is alkyl, amino or mono or disubstituted amino), methylenedioxy, hydroxy, halo, acylamino, amino, mono- or disubstituted amino, —CONR'R", —(alkylene)—CONR'R" (where R' and R" are hydrogen or alkyl), —COOR, —(alkylene)—COOR (where R is hydrogen or alkyl) or —$NRSO_2R'$ (where R is hydrogen or alkyl and R' is alkyl, amino, mono or disubstituted amino); and
$Ar^2$ is is a phenyl ring optionally substituted with one, two or three substituent(s) selected from alkyl, heteroalkyl, alkoxy, halo, trifluoromethyl, nitro, or monosubstituted or disubstituted amino.

21. The compound of claim 20 wherein:
$Ar^1$ is a phenyl ring optionally substituted with one, two or three substituents selected from methyl, methoxy, fluoro, chloro, dimethylamino, acetyl, acetylamino, hydroxy, amino, methylenedioxy, —$SO_2Me$, 2-acetylaminoethyl, 2-[(R)-amino-3-methylbutyrylamino]ethyl, 2-aminoethyl, aminomethyl, hydroxymethyl, aminocarbonyl, dimethylaminocarbonyl, —COOH, carboxymethyl, methoxycarbonylmethyl, aminocarbonylmethyl, dimethylaminocarbonylmethyl, acetylaminomethyl, methylsulfonylamino, methylsulfonylaminomethyl, dimethylaminosulfonyl-aminomethyl, or dimethylamino; and
$Ar^2$ is 3,4-difluorophenyl, 2,3-dichlorophenyl, 3,4-dichlorophenyl or 4-fluorophenyl.

22. The compound of claim 21 wherein $Ar^1$ is most preferably phenyl, 3-methoxyphenyl, 3-methylsulfonylphenyl, 3-dimethylaminophenyl, 3-acetylaminophenyl, 3-acetylphenyl, 3-[(2-acetylamino)ethyl]phenyl, 3-aminocarbonylphenyl, 4-dimethylaminocarbonylphenyl, 3-carboxyphenyl, 2,5-dimethoxyphenyl, 3,5-dimethoxy-phenyl, 3,4-dimethoxyphenyl, 3,4,5-trimethoxyphenyl, 3-aminocarbonylmethyl-phenyl, 3-acetylaminomethyphenyl, 3-carboxymethylphenyl, 3-methylsulfonyl-aminophenyl, 3-methylsulfonylaminomethylphenyl or 3-aminophenyl.

23. A pharmaceutical composition comprising a therapeutically effective amount of a compound of claim 1 and a pharmaceutically acceptable excipient.

24. A method of treatment of a disease in a mammal treatable by administration of a CCR-3 antagonist, comprising administration to the mammal of a therapeutically effective amount of a compound of claim 1.

25. The method of claim 24, wherein the disease is asthma.

26. A process for preparing a compound of claim 1, which comprises reacting a compound of Formula (II) where R, $R^1$, $R^2$ and $Ar^2$ are as defined in claim 1:

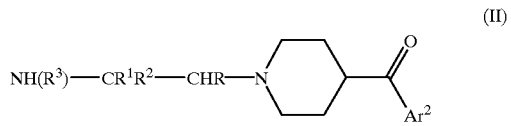

(II)

(i) with an acylating agent of formula $Ar^1$—Y—COL where L is a leaving group under acylating reaction conditions or an acid anhydride of formula $(Ar^1$—Y—$CO)_2O$ to provide a compound of Formula (I) where X is —C(O)N($R^3$)— wherein $R^3$ is hydrogen; or (ii) with an amine of formula $Ar^1$—Y—NH($R^4$) where $R^4$ is as defined in the Summary of the Invention, in the presence of a suitable coupling agent or an isocyanate of formula $Ar^1$—Y—N=C=O or a carbamoyl halide of formula $Ar^1$—Y—N($R^4$)—C(O)L where $R^4$ is as defined in the Summary of the Invention and L is a leaving group under acylating reaction conditions to provide a compound of Formula (I) where X is —N($R^4$)CON($R^3$)— wherein $R^3$ is hydrogen; or (iii) with an amine of formula $Ar^1$—Y—NH($R^4$) where $R^4$ is as defined in the Summary of the Invention, in the presence of a suitable coupling agent or an isothiocyanate of formula $Ar^1$—Y—N=C=S or a thiocarbamoyl halide of formula $Ar^1$—Y—N($R^4$)—C(S)L where $R^4$ is as defined in the Summary of the Invention and L is a leaving group to provide a compound of Formula (I) where X is —N($R^4$)C(S)N($R^3$)— wherein $R^3$ is hydrogen; or (iv) with a sulfonylating agent of formula $Ar^1$—Y—$SO_2L$ or $Ar^1$—Y—N($R^4$)—$SO_2L$ where $R^4$ is as defined in the Summary of the Invention and L is a leaving group under sulfonylating reaction conditions to provide a compound of Formula (I) where X is —$SO_2NR^3$— or —N($R^4$)$SO_2N(R^3)$— respectively, wherein $R^3$ is hydrogen; and (v) optionally converting a compound of Formula (I) prepared in Steps (i) to (iv) above, where $R^3$ is hydrogen to a compound of Formula (I) where $R^3$ is not hydrogen; and (vi) optionally converting the compound of Formula (I) prepared in Steps (i) to (v) above, to the corresponding acid addition salt by treatment with an acid.

* * * * *